United States Patent
Jacobs et al.

(10) Patent No.: US 7,751,050 B1
(45) Date of Patent: Jul. 6, 2010

(54) PHOTO SENSING FLUID CONTAMINATION AND QUALITY MONITOR

(75) Inventors: William A. Jacobs, Lake Worth, FL (US); Brian N. Nover, Wellington, FL (US); Allen D. Hertz, Boca Raton, FL (US)

(73) Assignee: MicroGlo, LLC

( * ) Notice: Subject to any disclaimer, the term of this patent is extended or adjusted under 35 U.S.C. 154(b) by 0 days.

(21) Appl. No.: 12/235,591

(22) Filed: Sep. 22, 2008

Related U.S. Application Data

(60) Division of application No. 12/211,595, filed on Sep. 16, 2008, which is a continuation-in-part of application No. 11/150,325, filed on Jun. 11, 2005, now Pat. No. 7,427,153, which is a continuation-in-part of application No. 10/227,666, filed on Aug. 26, 2002, now Pat. No. 6,905,237.

(51) Int. Cl.
*G01N 21/00* (2006.01)
*G01B 9/02* (2006.01)

(52) U.S. Cl. .................... 356/436; 356/440; 356/246; 250/576; 436/165

(58) Field of Classification Search .................. 356/436
See application file for complete search history.

(56) References Cited

U.S. PATENT DOCUMENTS

| | | | | |
|---|---|---|---|---|
| 4,549,809 A | * | 10/1985 | Minekane et al. | ........... 356/436 |
| 6,016,372 A | * | 1/2000 | Fein et al. | ..................... 385/12 |
| 6,437,345 B1 | * | 8/2002 | Bruno-Raimondi et al. | ...... 250/458.1 |
| 6,526,188 B2 | * | 2/2003 | Dourdeville et al. | .......... 385/12 |
| 6,580,507 B2 | * | 6/2003 | Fry et al. | ..................... 356/436 |
| 6,942,773 B1 | * | 9/2005 | Olivares et al. | ............. 204/452 |
| 7,034,933 B2 | * | 4/2006 | Walker et al. | ................ 356/246 |
| 7,298,472 B2 | * | 11/2007 | Gerner et al. | ................ 356/246 |
| 7,554,673 B2 | * | 6/2009 | Kiesel et al. | ................. 356/519 |

\* cited by examiner

*Primary Examiner*—Gregory J Toatley, Jr.
*Assistant Examiner*—Rebecca C Slomski
(74) *Attorney, Agent, or Firm*—Allen D. Hertz

(57) ABSTRACT

A fluid quality monitoring apparatus (100) comprising a fluid flow channel (120) having a photo sensing material (104) disposed upon a first surface and a light source emitting light (132) through an opposing light transitive surface (106). The condition of the fluid affects the absorption and reflection of the light. The penetrating light is received by the photo sensing material (104), which provides an output that can be utilized to analyze the condition of the fluid. The light can be provided via a plurality of LEDS, the incorporation of a radially distributed series of fiber optic strands, or any other light source. The sensing material can include defraction gratings, improving the monitoring process. The sensing material can be incorporated in a variety of configurations. The apparatus is preferably designed to be integrated between a fluid filter and the respective filter mounting bracket.

19 Claims, 21 Drawing Sheets

PHOTO SENSING FLUID CONTAMINATION AND QUALITY MONITOR

RELATED US PATENT APPLICATION

This Continuation-In-Part Patent Application claims priority to Non-Provisional U.S. application Ser. No. 11/150,325, filed Jun. 11, 2005, scheduled to issue as U.S. Pat. No. 7,427,153 on Sep. 23, 2008; which claims priority to utility application Ser. No. 10/227,666, filed Aug. 26, 2002, now U.S. Pat. No. 6,905,237 issued on Jun. 14, 2005; and is a Divisional Application of Non-Provisional U.S. application Ser. No. 12/211,595, filed Sep. 16, 2008; all of which are incorporated by reference herein.

BACKGROUND OF THE INVENTION

1. Field of the Invention

The present invention relates to a fluid quality monitor and more specifically to a device and method using a photosensitive material for monitoring the quality of and amount of contamination within a fluid or lubricant.

2. Discussion of the Related Art

This invention relates to fluid monitoring devices and method, which are generally used in monitoring of lubricants, fuel, sewage, and the like. More particularly, the present invention projects a light emission through the subject fluid towards a photosensitive material. The photosensitive material detects the amount of light that is passed through the subject fluid. The apparatus then utilizes this information to interpret the quality of the fluid.

Fluid disposed within a system is normally monitored via a pressure sensor and a temperature sensor. The fluids are subjected to a filtration system to remove any impurities within the fluid. A pressure monitoring system can inform the operator if the filter is becoming obstructed.

Dielectric constant is measured using a capacitance sensor.

The viscosity can be measured using either a rheometer or a viscometer.

Particle count can be measured via any number of ways, such as providing a sonic or ultrasonic frequency between two frequency probes, which monitor the normal pulse to detect any deviation of that pulse. The deviation can be used to calculate the quantity or volume of contaminating particulate matter.

Wear metals are monitored via a variety of sensors. One such sensor is a ferrous sensor using electromagnets. This process is normally provided external to the normal lubricant fluid flow environment or closed loop system.

Water entrapment can be monitored via an impedance measurement or capacitance measurement of the dielectric constant.

The total base number (TBN) can be monitored. The TBN is a measure of a lubricant's reserve alkalinity. It is measured in milligrams of potassium hydoxide per gram (mg KOH/g). The TBN determines how effective the control of acids formed will be during the combustion process. The higher the TBN, the more effective it is in suspending wear-causing contaminants and reducing the corrosive effects of acids over an extended period of time.

The associated measurement ASTM D2896 and ASTM D4739-06 generally range from 6-80 mg KOH/g in modern lubricants, 7-10 mg for general automotive use and 10-15 for Diesel operations.

Marine grade lubricants generally will run from 15-50 mgKOH/g, but can be as high as 70 or 80 mg KOH/g as is the case of Exxon's MobileGuard 570 or respectively Castrol's Cyltech 80AW this high level is designed to allow a longer operating period between changes, under harsh operating conditions. When the TBN is measured at 2 mg KOH/g or less the lubricant is considered inadequate for engine protection, and is at risk for allowing corrosion to take place. Higher sulfur fuel will decrease the TBN faster due to the increased formation of sulfuric acid.

The TBN is normally measured off line, reducing the ability to identify a critical level that would need servicing.

Planar laser-induced fluorescence (PLIF) is an optical diagnostic technique widely used for flow visualization and quantitative measurements. PLIF has been shown to be used for velocity, concentration, temperature and pressure measurements. A typical PLIF setup consists a source of light (usually a laser), an arrangement of lenses to form a sheet, fluorescent medium, collection optics and a detector. The light from the source illuminates the medium, which then fluoresces. This signal is captured by the detector and can be related to the various properties of the medium.

The typical lasers used as light sources are pulsed, which provide a higher peak power than the continuous-wave lasers. Also the short pulse time is useful for good temporal resolution. Some of the widely used laser sources are Nd:YAG laser, dye lasers, excimer lasers, and ion lasers. The light from the laser (usually a beam) is passed through a set of lenses and/or mirrors to form a sheet, which is then used to illuminate the medium. This medium is either made up of fluorescent material or can be seeded with a fluorescent substance. The signal is usually captured by a CCD or CMOS camera (sometimes intensified cameras are also used). Timing electronics is often used to synchronize pulsed light sources with intensified cameras.

In optics, a collimator may consist of a curved mirror or lens with some type of light source and/or an image at its focus. Collimators may be used with laser diodes and CO2 cutting lasers. Proper collimation of a laser source with long enough is coherence length can be verified with a shearing interferometer.

Fiber Bragg grating (FBG) is a type of distributed Bragg reflector constructed in a short segment of optical fiber that reflects particular wavelengths of light and transmits all others. This is achieved by adding a periodic variation to the refractive index of the fiber core, which generates a wavelength specific dielectric mirror. A fiber Bragg grating can therefore be used as an inline optical filter to block certain wavelengths, or as a wavelength-specific reflector.

Etched gratings such as those taught by U.S. Pat. No. 6,522,795 teach etching grooves or recessions (gratings) in an upper surface of a material to provide a controllable refractive index. The grating can be provided via a first and second cladding. If the index of the second cladding is different from that of the first cladding, the configuration of the first cladding provides an optical grating. If, however, the controllable index of the second cladding is adjusted to equal that of the first cladding, the grating becomes essentially transparent. This grating is particularly useful as a reconfigurable add/drop filter in a WDM optical communication system. It is also useful in grating-assisted couplers and variable optical delay lines.

Thus, what is desired is a fluid quality monitoring system that monitors the amount of contamination as well as any degradation.

SUMMARY OF THE INVENTION

The present invention is directed to a fluid quality monitoring system comprising a fluid flow channel having an illumination source on a first side and a photosensitive material disposed along an opposing side, wherein the monitoring system monitors and correlates the change in light received by the photosensitive material to the quality of the monitored fluid. The term fluid should be considered as representative of a liquid or a gas, unless otherwise specified.

In a first aspect of the present invention, a fluid quality monitoring apparatus is defined comprising:

a fluid passage having a first wall and an opposing wall spanning between a fluid inlet port and a fluid exit port;

a photosensitive material disposed upon said first wall;

an illumination source providing light through at least one of the first wall and the opposing wall directed at least one of directly and indirectly towards the photosensitive material; and an output conduit providing an output from photosensitive material.

While another aspect of the present invention configures the fluid passage about a perimeter of the fluid quality monitoring apparatus.

With another aspect of the present invention configures the illumination source within a central location, having the fluid passage about the perimeter of the fluid quality monitoring apparatus. The illumination source can be an LED, a laser LED, a plurality of LEDs, an incandescent bulb, a light source connected to a plurality of radially arranged fiber optic fibers and the like.

Yet another aspect incorporates a light directing shield placed about the light source; the light-directing shield directing the illumination towards the fluid passage.

Wherein another aspect incorporates at least one fluid passage through the light source region of the apparatus.

Another aspect incorporates a fluid driven generator, the generator providing power to at least one of the light source and the photosensitive material.

In another aspect, the casing is designed to interface with a common lubricant, oil, or fuel filter.

While another aspect provides an intermediate photo sensing material layer.

These and other features, aspects, and advantages of the invention will be further understood and appreciated by those skilled in the art by reference to the following written specification, claims and appended drawings, which follow.

BRIEF DESCRIPTION OF THE DRAWINGS

For a fuller understanding of the nature of the present invention, reference should be made to the accompanying drawings in which.

Like reference numerals refer to like parts throughout the several views is of the drawings.

DETAILED DESCRIPTION OF REPRESENTATIVE EMBODIMENTS

Figure 1:
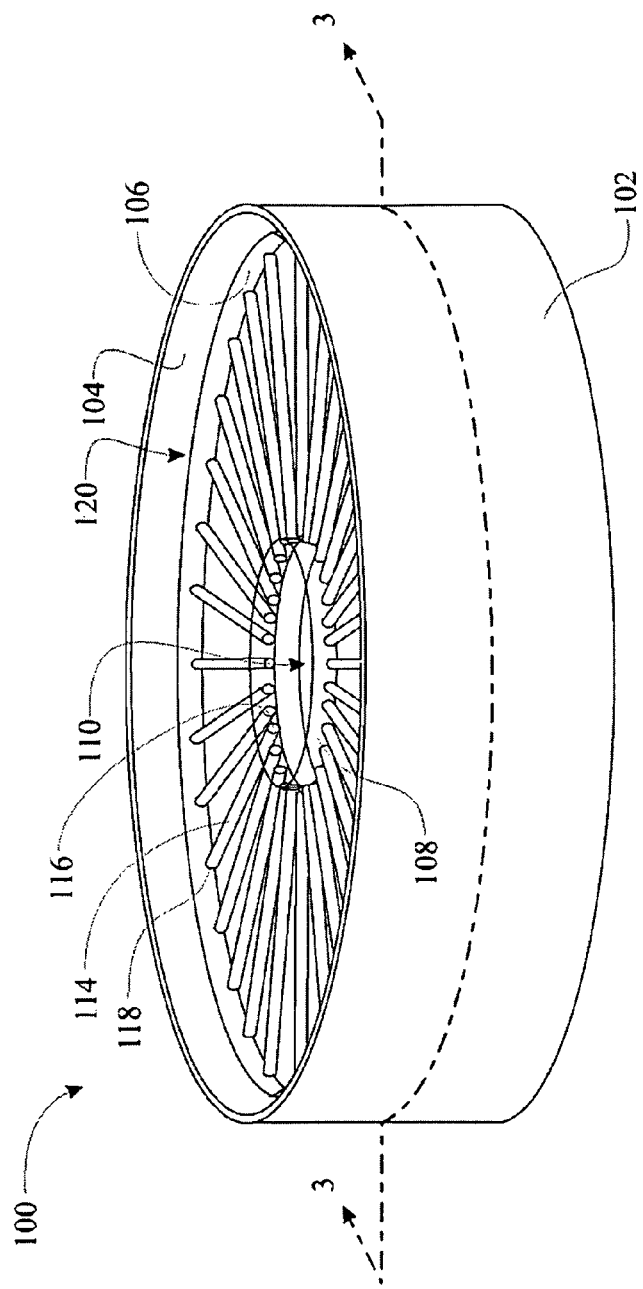
FIG. 1 presents an isometric view of a first exemplary embodiment of the a fluid quality monitoring apparatus utilizing a radially arranged fiber optic light distribution configuration.

For purposes of description herein, the terms "upper", "lower", "left", "rear", "right", "front", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 2:
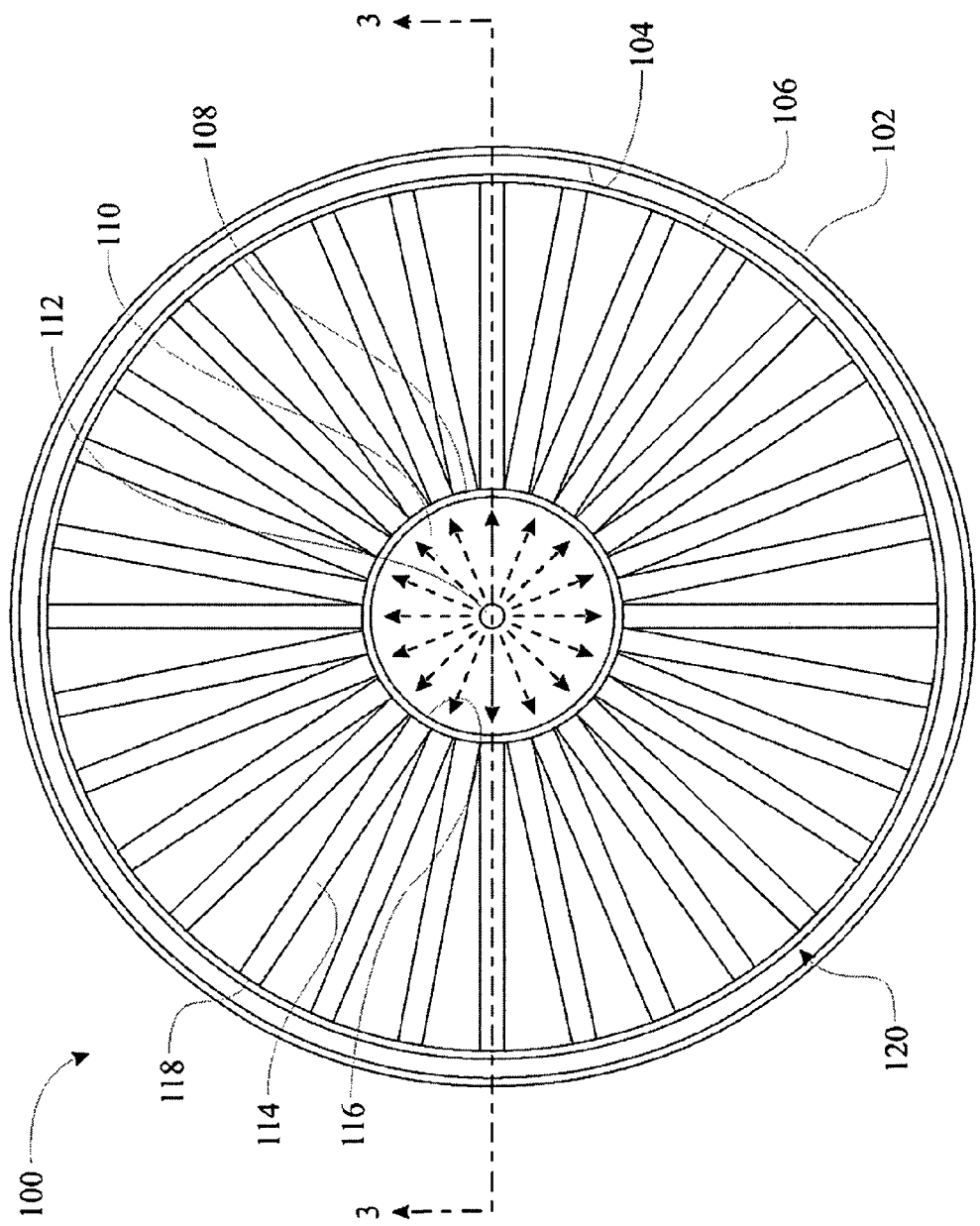
FIG. 2 presents a top planar view of the fluid quality monitoring apparatus initially illustrated in FIG. 1.
Figure 3:
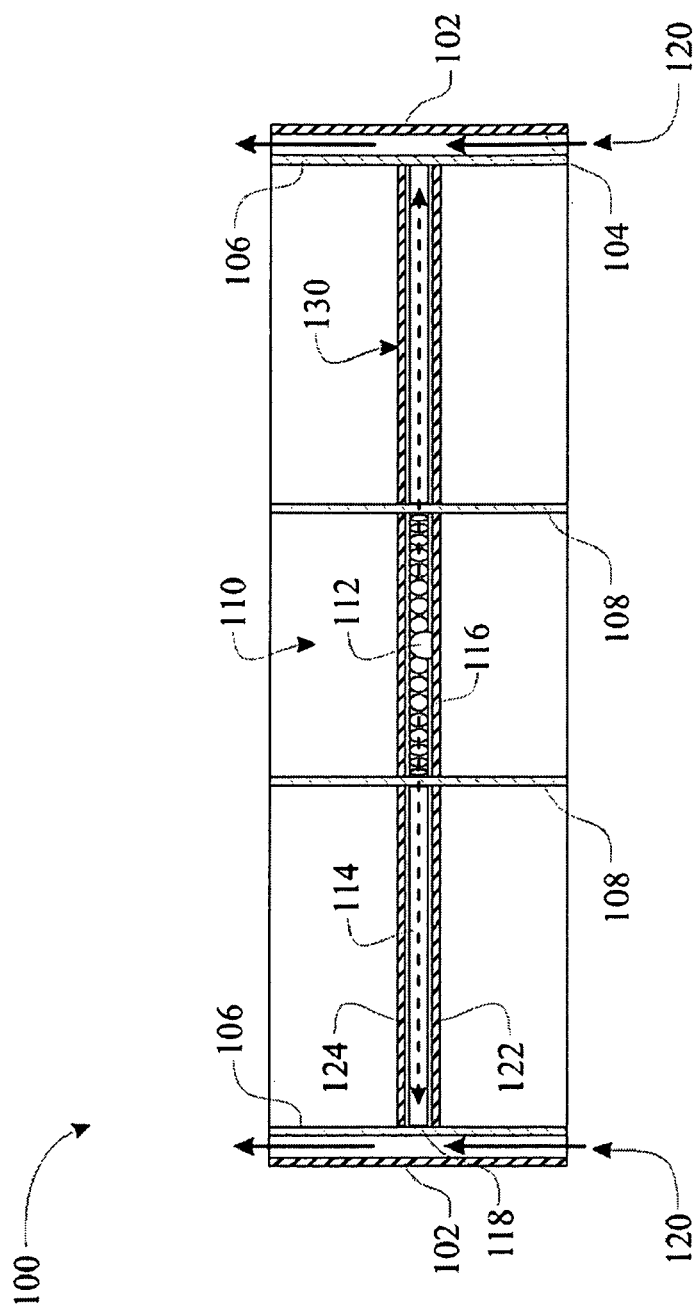
FIG. 3 presents a sectional view of the fluid quality monitoring apparatus taken along sectioning line 3-3 of FIG. 2.

The present invention utilizes a fluid conduit having a photosensitive material disposed along a first side and a light source directed through the fluid conduit and towards the photosensitive material. Several embodiments are presented herein, with a first embodiment being shown in FIGS. 1 through 3, being referred to as a fluid condition photovoltaic monitoring apparatus 100. The fluid condition photovoltaic monitoring apparatus 100 is assembled having an apparatus casing 102 (preferably being an outer tubular structure) with a photo receptive surface 104 laminated to an interior surface and an illumination distribution assembly 130 (preferably being an inner tubular structure) forming a fluid monitoring flow channel 120 there between. An entrance port is provided at one end and an exit port is provided at an opposing end of the fluid monitoring flow channel 120. It is understood that a coupling system is integrated into the apparatus 100 to provide a fluid conduit between the fluid source, the fluid monitoring flow channel 120, and returning to the fluid system. The illumination distribution assembly 130 provides an illumination source directing light towards the photo receptive surface 104. Fluid flowing through the fluid monitoring flow channel 120 absorbs or reflects a portion of the light, is resulting in a lower light intensity level identified by the photo receptive surface 104. The photo receptive surface 104 provides an output identifying the wattage (or other measurement) of the sensed light levels or intensity.

One measure of total power of light emitted is referred to as radiant flux. A common unit of measure is referred to as a watt. Alternately, a lumen is another unit of measure, more specifically applied to luminous flux, a measure of the perceived power of light. Luminous flux differs from radiant flux, the measure of the total power of light emitted, in that luminous flux is adjusted to reflect the varying sensitivity of the human eye to different wavelengths of light.

The illumination distribution assembly 130 can be selected from a wide variety of illuminating configurations, with several being presented within this disclosure. A first exemplary embodiment utilizing a radially arranged fiber optic strands is presented in FIGS. 1 through 5. A plurality of fiber optic strand 114 are disposed between an illumination management lower substrate 122 and an illumination management upper substrate 124 and are arranged having a fiber optic light source end 116 positioned adjacent a light source region 110 and oriented extending radially outward from the light source region 110, placing a fiber optic light emitting end 118 adjacent to a translucent light emitting wall 106 (alternately referred to as an inner tubular structure). The translucent light emitting wall 106 forms a wall of the fluid monitoring flow channel 120. The preferred translucent light emitting wall 106 is translucent and provides a circular wall internally positioned adjacent to the photo receptive surface 104, thus providing light to the fluid monitoring flow channel 120 and the photo receptive surface 104. At least one illumination source 112 is to assembled within a light source region 110 and in optical communication with the translucent light emitting wall 106. The illumination source 112 can be any form of light emitting device, including an LED, a laser LED, an incandescent bulb, and the like. In the exemplary embodiment, a plurality of fiber optic strand 114 is radially arranged providing a conduit for the light. The illumination management lower substrate 122 and illumination management upper substrate 124 can provide a sealed environment for the light source region 110, aiding and extending the long-term reliability of the illumination source 112. In some embodiments, the opposing surfaces of the illumination management lower substrate 122 and the illumination management upper substrate 124 can have a reflective surface for aiding in any transfer of light. The light enters the fiber optic light source end 116, travels through the fiber optic strand 114 and exits through the fiber optic light emitting end 118. The light continues through the translucent material of the translucent light emitting wall 106. The fiber optic light source end 116 can be located adjacent an illumination source distribution wall 108, the illumination source distribution wall 108 providing a fluid barrier between the light source region 110 and other sections. This configuration allows for fluid passage ways to the incorporated passing fluid through the illumination management lower substrate 122 and the illumination management upper substrate 124.

Figure 4:
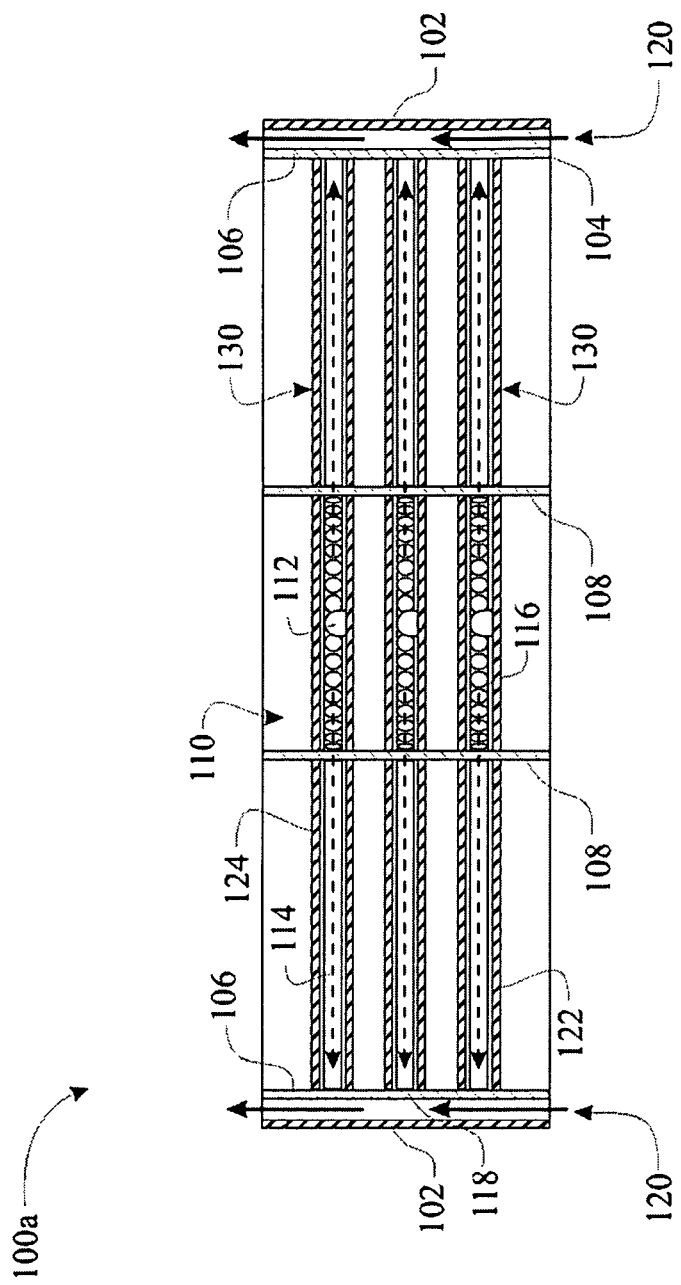
FIG. 4 presents a sectional view of a fluid quality monitoring apparatus similar to the apparatus of FIG. 3, incorporating additional illumination distribution assemblies.

A plurality of illumination distribution assemblies 130 can be incorporated such as via a stacking configuration illustrated in FIG. 4. By incorporating a plurality of illumination distribution assemblies 130, the system increases the total amount of emitted light, thus increasing the accuracy of the monitored quality determined by the photo receptive surface 104. Each illumination distribution assembly 130 or the plurality of illumination distribution assemblies 130 can be isolated from any fluid via the illumination management lower substrate 122 and illumination management upper substrate 124 and at least one vertical member disposed there between.

Figure 5:
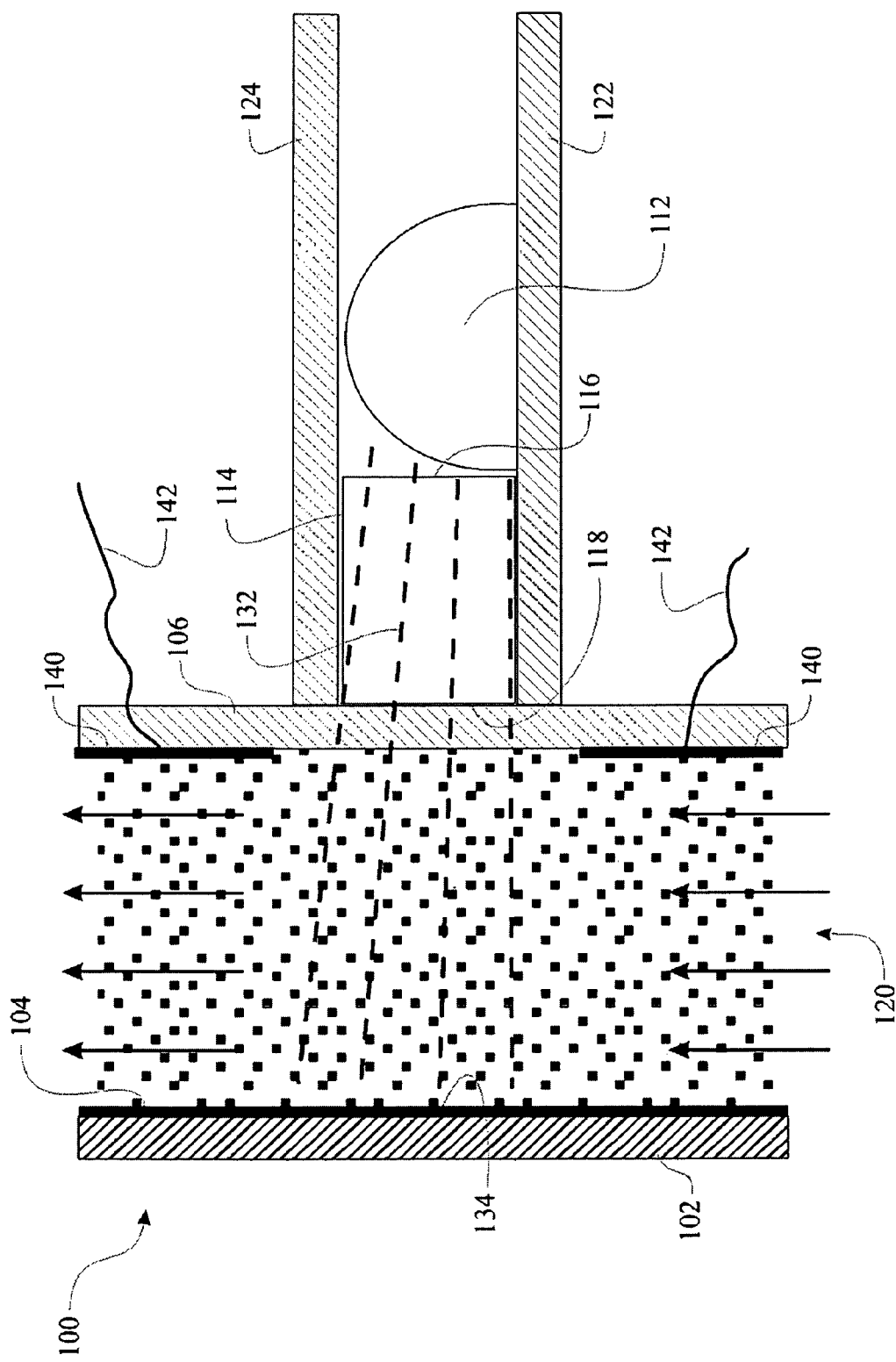
FIG. 5 presents a magnified sectional view of the fluid quality monitoring apparatus of FIG. 3 illustrating details of the photosensitive monitoring configuration.

The functionality of the fluid condition photovoltaic monitoring apparatus 100 is represented in an enlarged view illustrated in FIG. 5. The emitted light 132 is emitted by an illumination source 112. The emitted light 132 can be transferred, entering a fiber optic light source end 116, passing through a fiber optic strand 114 and exiting a fiber optic light emitting end 118. The emitted light 132 continues through the translucent light emitting wall 106, entering into the fluid monitoring flow channel 120, and passing through the fluid. As the emitted light 132 passes through the fluid, the emitted light 132 is partially absorbed, reflected, and reduced in other means. The emitted light 132 projects upon the photo receptive surface 104 becoming a received light 134. The photo receptive surface 104 provides an output (such as a voltage or current) indicating the amount or power of light received. The output can be in a peak measurement, an RMS measurement, a waveform, digital, analog, and the like. The output would generally be communicated to a processing device which can be integrated into the apparatus fluid condition photovoltaic monitoring apparatus 100, isolated from the fluid condition photovoltaic monitoring apparatus 100, or partially distributed between both. The determined results can be presented to an operator via any known means, including visual, audio, data recording, local or remotely, and the like. The photo receptive surface 104 can provide an electrical output via electrical conductors (not shown, but well understood in the solar industry). Additionally, a secondary photo receptive surface 140 can be disposed on the channel side of the translucent light emitting wall 106 registering any reflected light. The secondary photo receptive surface 140 would be preferably the same material as the photo receptive surface 104, and include a power and signal conductor 142 providing the electrical conductors as previously described. The electrical conductors power and signal conductor 142 can be wires, a copper trace laminated to the assembly, and the like. This concept can be applied to the other configurations presented herein.

Figure 6:
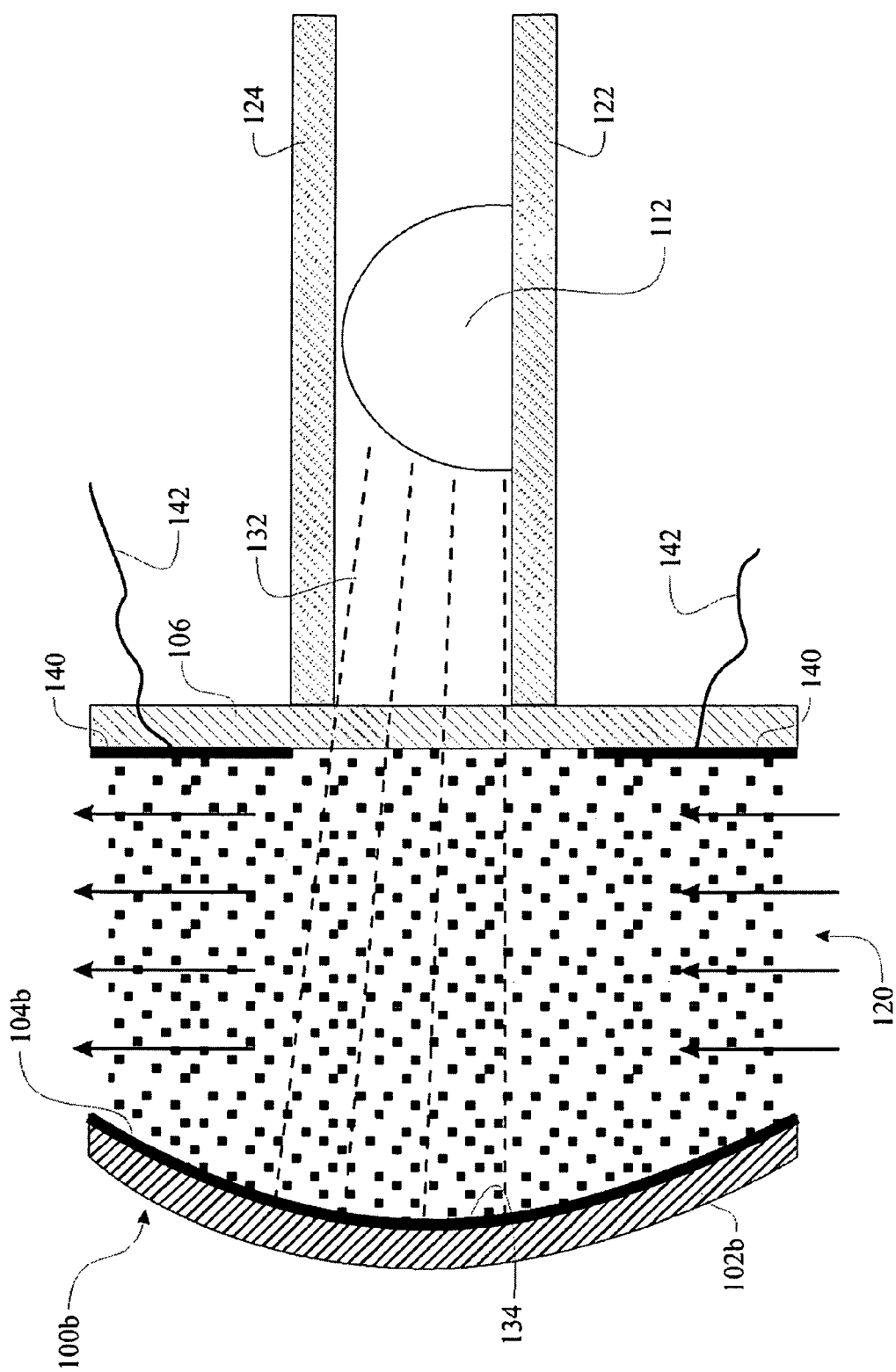
FIG. 6 presents an alternate embodiment of the fluid quality monitoring apparatus as illustrated in FIG. 5, incorporating an arched photosensitive monitoring configuration.

An enhanced embodiment is best illustrated in FIG. 6, referred to as a fluid condition photovoltaic monitoring apparatus 100b. The apparatus casing 102 is arched and referred to as an apparatus casing 102. The illustration presents a concave arch respective to the fluid passage way. This configuration slows the fluid flow in the monitored region of the fluid condition photovoltaic monitoring apparatus 100b. Alternately, the arch can be convex, increasing the fluid flow through the narrow clearance. The disclosure presents an outer tubular structure that is not is parallel with the inner tubular structure, providing a change in flow rates.

Figure 7:
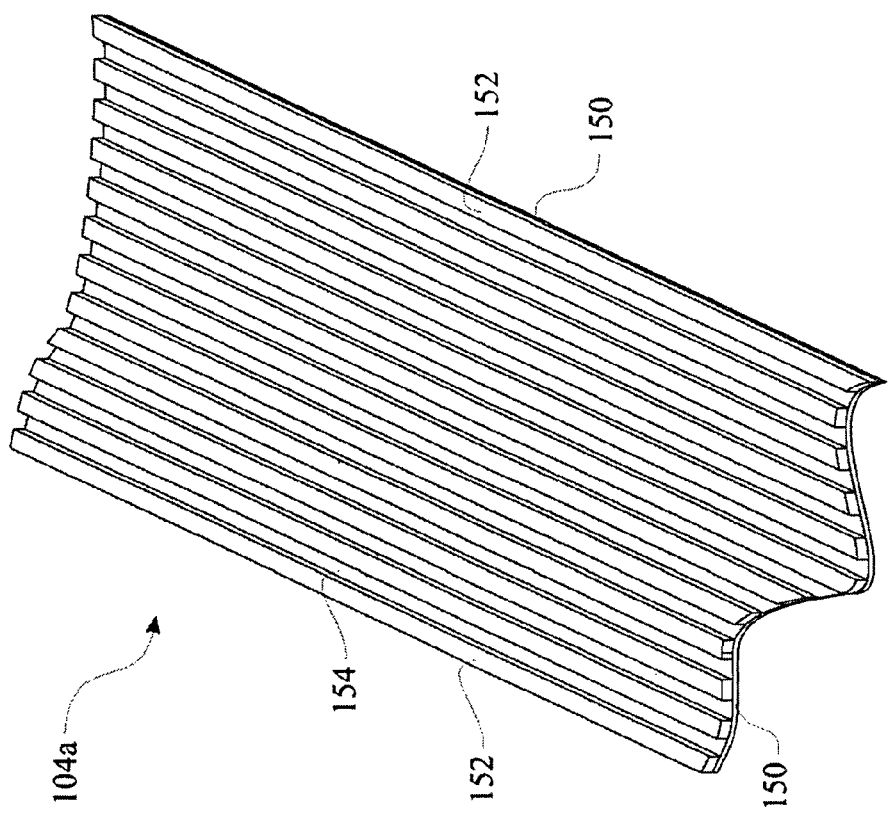
FIG. 7 presents a detailed view of a first optional surface texture of a photosensitive material.
Figure 8:
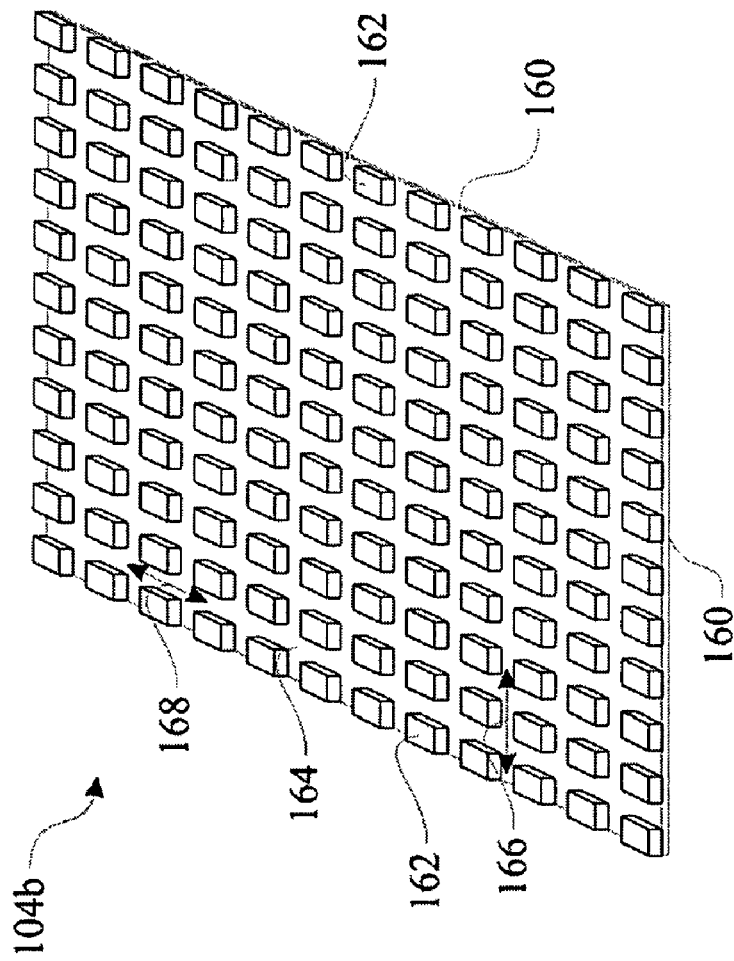
FIG. 8 presents a detailed view of a second optional surface texture of a photosensitive material.
Figure 9:
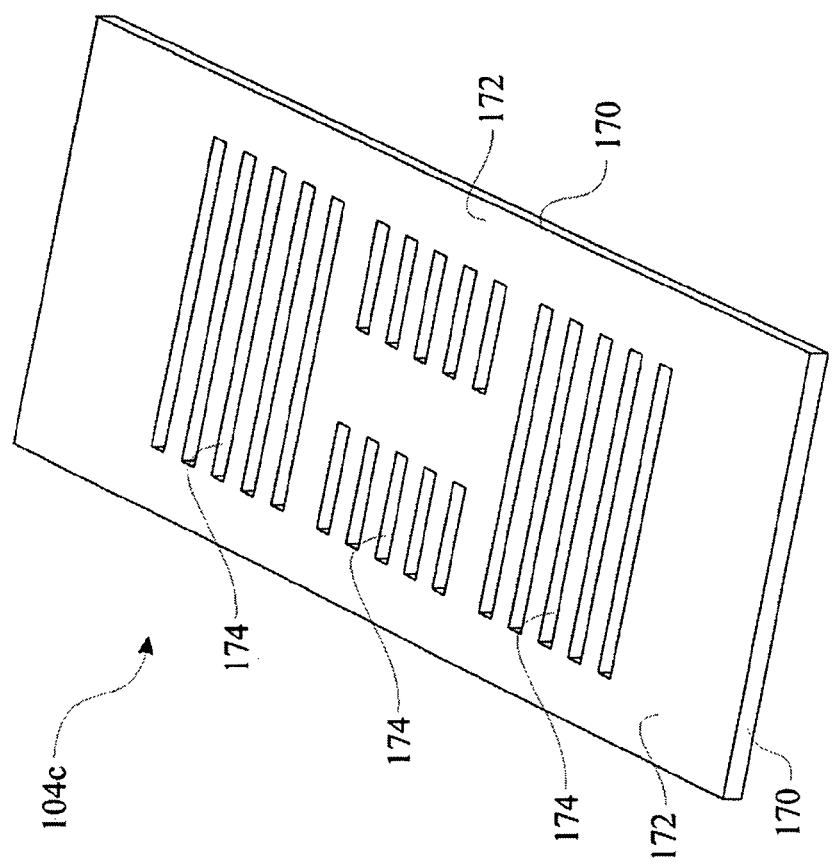
FIG. 9 presents a detailed view of a second optional surface texture of a photosensitive material.
Figure 10:
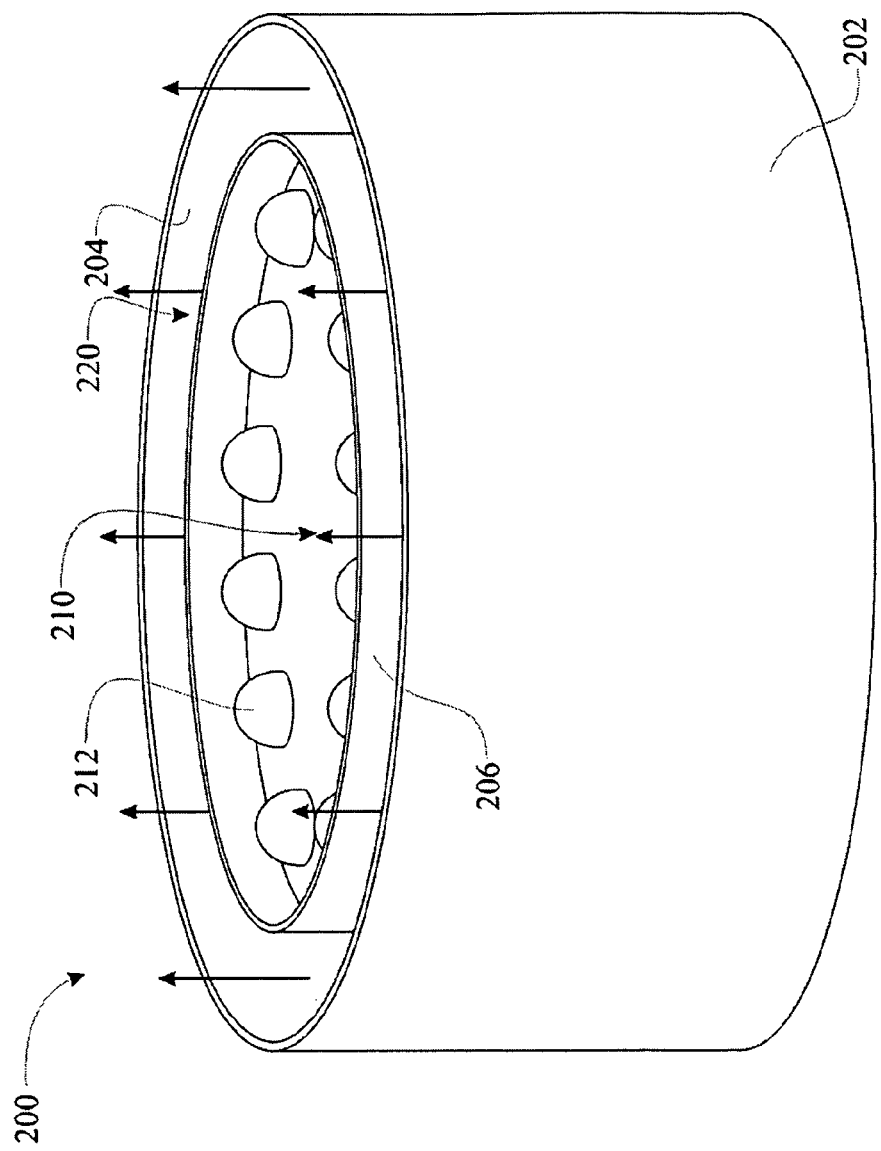
FIG. 10 presents an isometric view of a second exemplary embodiment of the a fluid quality monitoring apparatus utilizing a plurality of illuminating sources.
Figure 11:
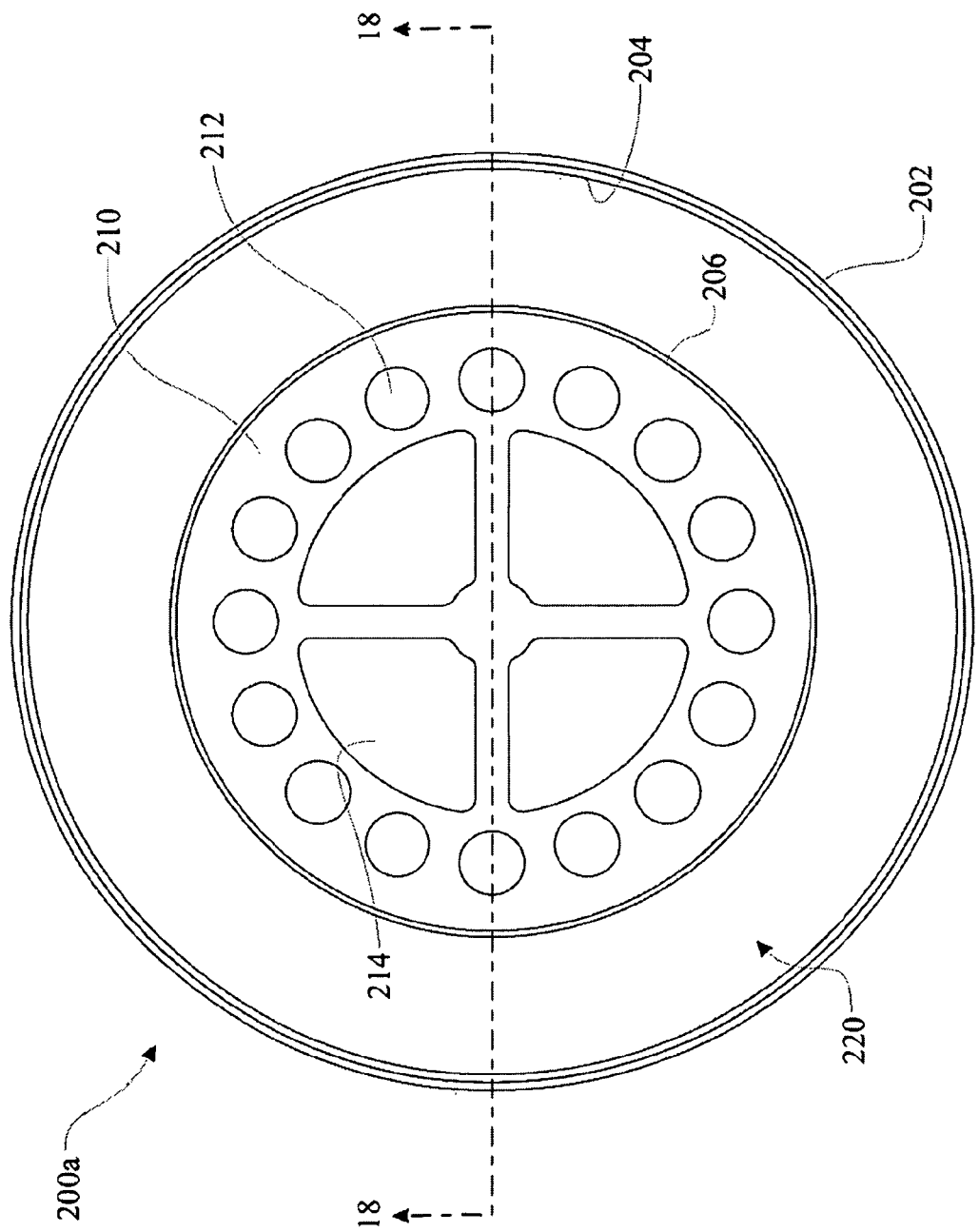
FIG. 11 presents a top planar view of the fluid quality monitoring apparatus initially illustrated in FIG. 10.
Figure 12:
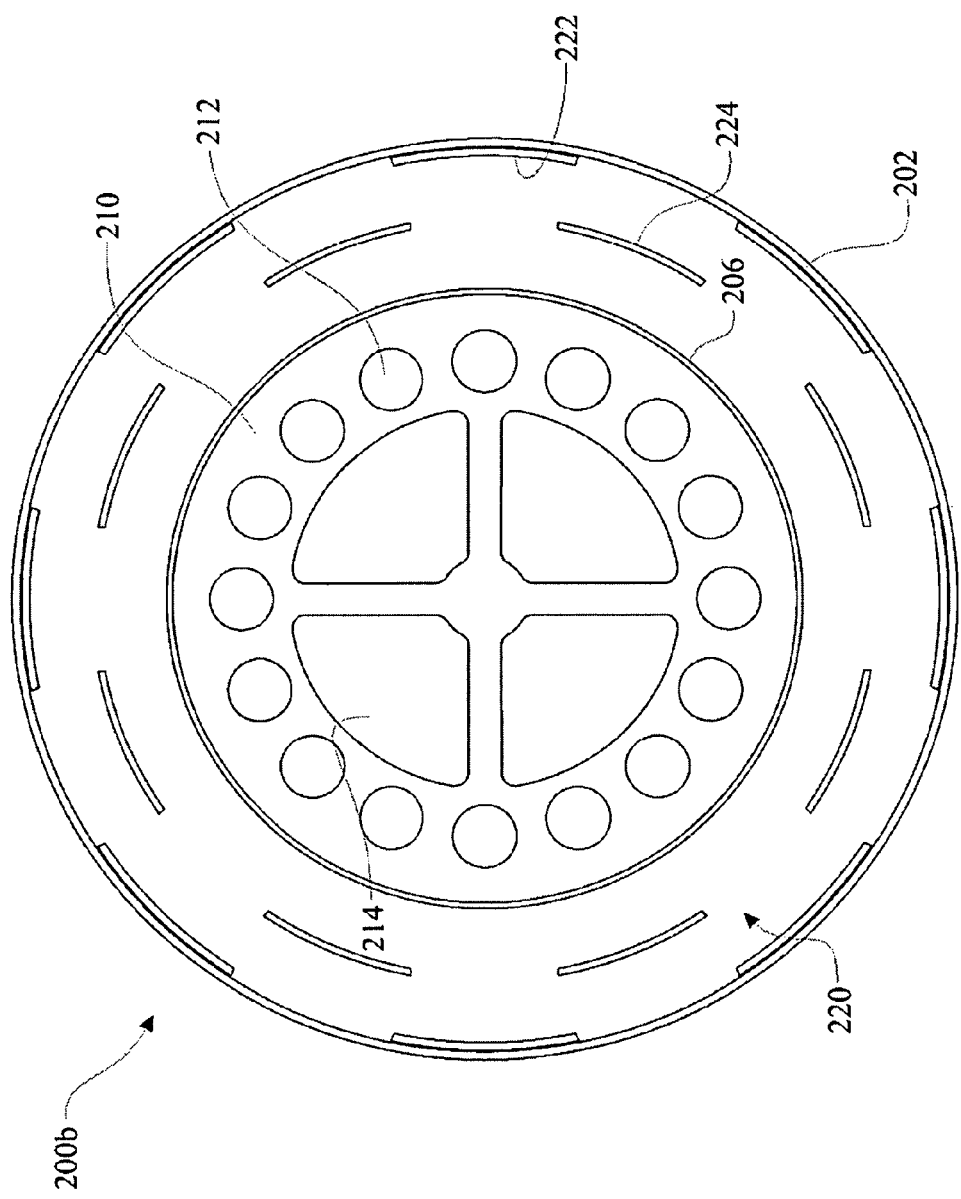
FIG. 12 presents a top planar view of the fluid quality monitoring apparatus similar to the monitor of FIG. 10, additionally incorporating an intermediate photosensitive layer.

The photo receptive surface 104 can be textured such as the two exemplary embodiments presented as photo receptive surface 104a of FIG. 7, as photo receptive surface 104b of FIG. 8, and as photo receptive surface 104c of FIG. 9. The texturing (sometimes referred to as diffraction grating) provides improved flow control, thus more consistent monitored results. A first texturing embodiment 104a (FIG. 7) provides a plurality of longitudinal ridges 152 disposed upon a photosensitive base material 150 in a longitudinal array. A longitudinal grooves 154 results between each adjacent longitudinal ridge 152. The fluid passes through the longitudinal grooves 154 in a laminar flow. A second texturing embodiment 104b (FIG. 8) provides a plurality of frequency controlling ridges 162 disposed upon a photosensitive base material 160 in a lateral and a longitudinal array. The array of frequency controlling ridges 162 expose the photosensitive base material 160 forming frequency controlling troughs 164 (a frequency controlling trough rows 166 and a frequency controlling trough columns 168) between each adjacent frequency controlling ridges 162. The fluid passes through the frequency controlling trough rows 166 and the frequency controlling trough columns 168 in a laminar flow. Although two patterns are presented, it is understood that any pattern can be utilized providing or optimizing the flow across the photosensitive surface 150, 160. A third texturing embodiment 104c (FIG. 9) provides a photosensitive base material 170 having a plurality of frequency controlling apertures 174 formed through the photosensitive base material 170. A photosensitive surface 172 of the photosensitive base material 170 absorbs the emitted light.

A second exemplary embodiment is shown in FIGS. 10 through 15, being referred to as a fluid condition photovoltaic monitoring apparatus 200. The fluid condition photovoltaic monitoring apparatus 200 is assembled having an apparatus casing 202 with a photo receptive surface 204 laminated to an interior surface and a translucent light emitting wall 206 forming a fluid monitoring flow channel 220 there is between. The light source region 210 provides an illumination source directing light through the translucent light emitting wall 206 and towards the photo receptive surface 204. Fluid flowing through the fluid monitoring flow channel 220 absorbs or reflects a portion of the light, resulting in a lower light intensity level identified by the photo receptive surface 204. The photo receptive surface 204 provides an output identifying the wattage (or other measurement) of the sensed light levels or intensity. The light source region 210 provides a platform for mechanically maintaining and electrically operating a plurality of illumination source 212. The illumination sources 212 are located adjacent the interior edge of the translucent light emitting wall 206. An interior flow port 214 can be formed through the light source region 210, allowing fluid to pass through the light source region 210. The illumination source 212 can be exposed to the fluid or preferably encapsulated or isolated from the fluid. The interior flow ports 214 can include sidewalls, passing fluid through a sealed section, isolating the fluid from the illumination source 212. The interior flow ports 214 can be in any geometry conducive to the fluid flow and shape of the light source region 210.

Additional features are presented throughout the figures. One such feature incorporates an intermediate spaced photo receptive surface 224. The intermediate spaced photo receptive surface 224 is disposed within a central region of the fluid monitoring flow channel 220. The photo receptive surface 204 can be segmented, being presented as a distal spaced photo receptive surface 222. This configuration provides variations in the photosensitive monitored results. Several variations of the spacing, design, and the like can be utilized, both parallel and perpendicular to the direction of flow. The distal spaced photo receptive surface 222 and intermediate spaced photo receptive surface 224 can include apertures, or other shapes.

Another optional feature (FIG. 13) incorporates a control sample 230 having a boundary formed via a pair of control sample enclosure 232, a portion of the translucent light emitting wall 206, and a portion of the apparatus casing 202. The control sample enclosure 232 would contain a control of the subject fluid. It would be preferred that the control sample 230 is formed incorporating a portion of each of the monitoring systems, such as the distal spaced photo receptive surface 222 and the intermediate spaced photo receptive surface 224 illustrated herein. This configuration exposes each of the monitoring portions to the control fluid.

Figure 13:
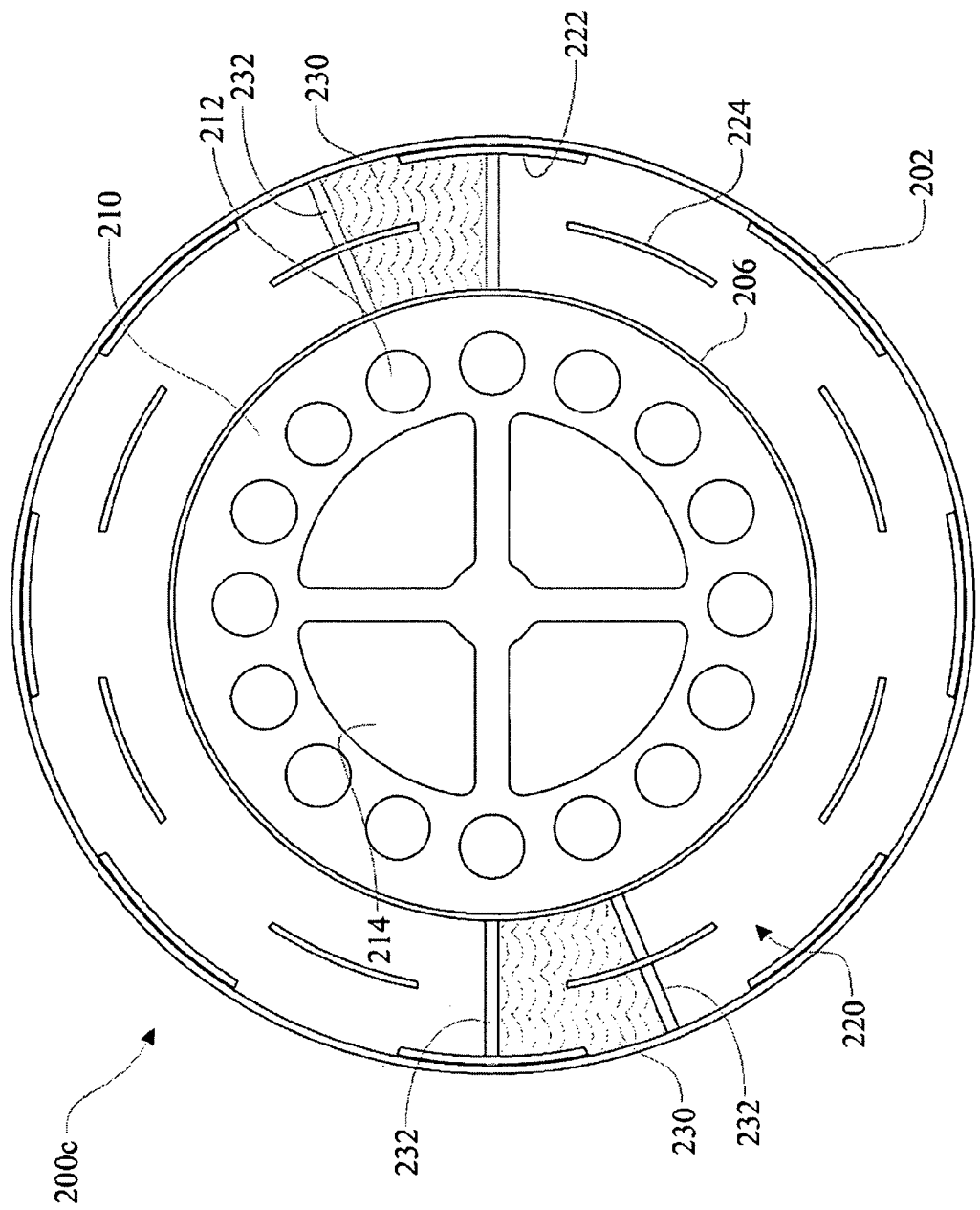
FIG. 13 presents a top planar view of the fluid quality monitoring apparatus similar to the monitor of FIG. 12, additionally incorporating a control is specimen containing section.
Figure 14:
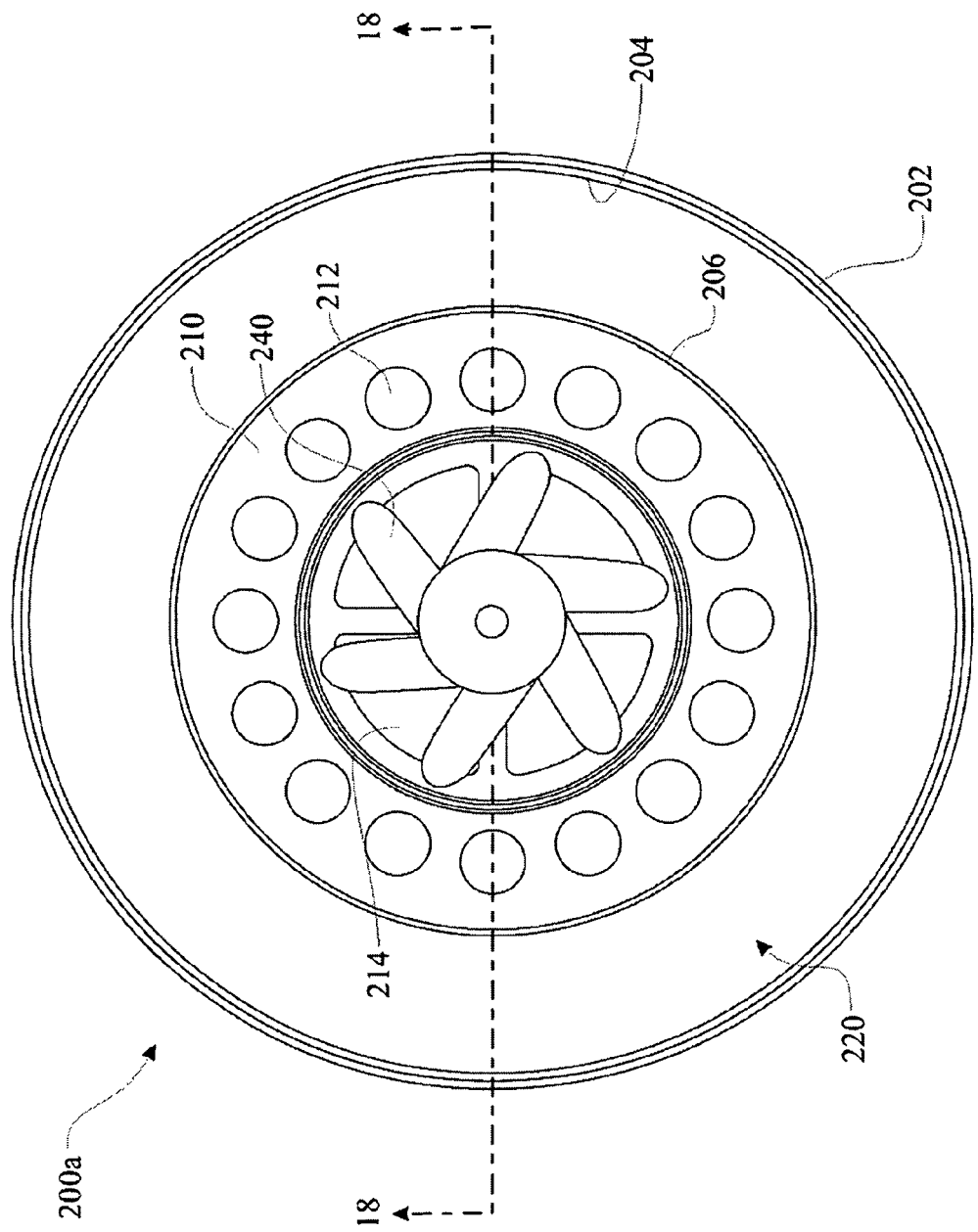
FIG. 14 presents a top planar view of the fluid quality monitoring apparatus similar to the monitor of FIG. 11, additionally incorporating a flow driven power generator.
Figure 15:
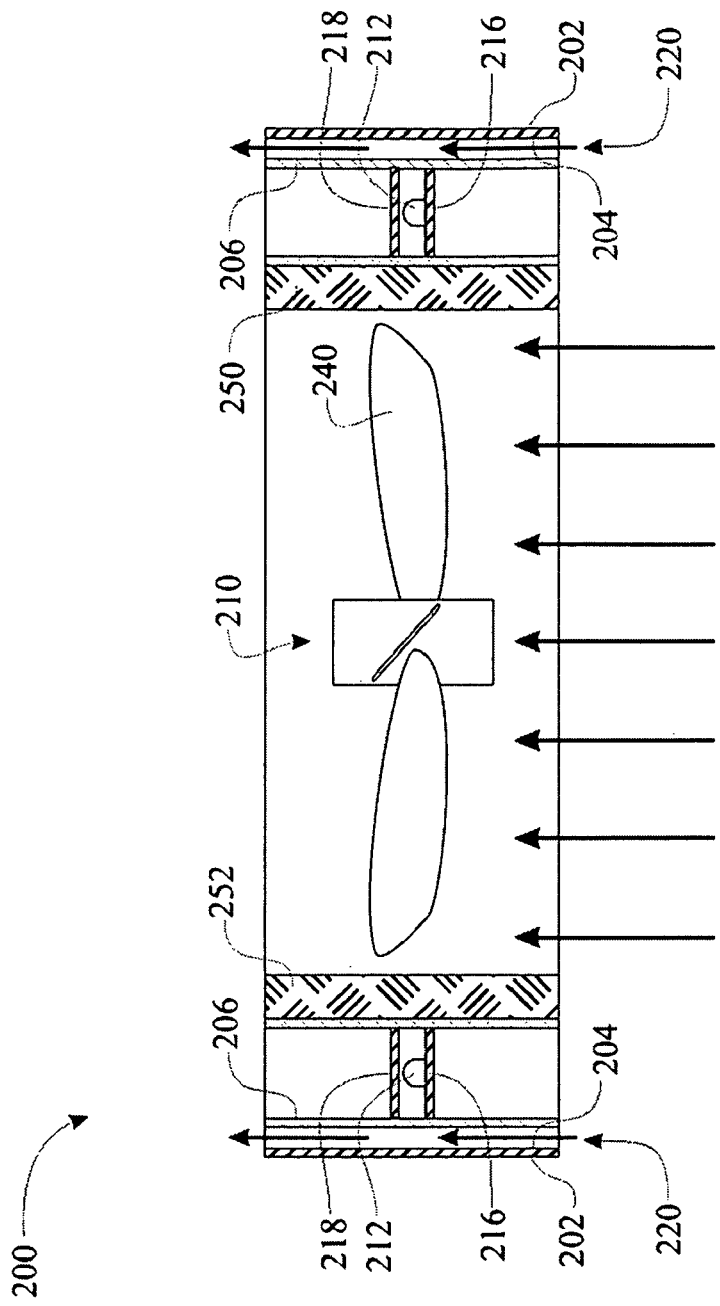
FIG. 15 presents a sectional side view of a fluid quality monitoring apparatus similar to the monitor of FIG. 14, illustrating a first exemplary embodiment of the flow driven power generator configuration.
Figure 16:
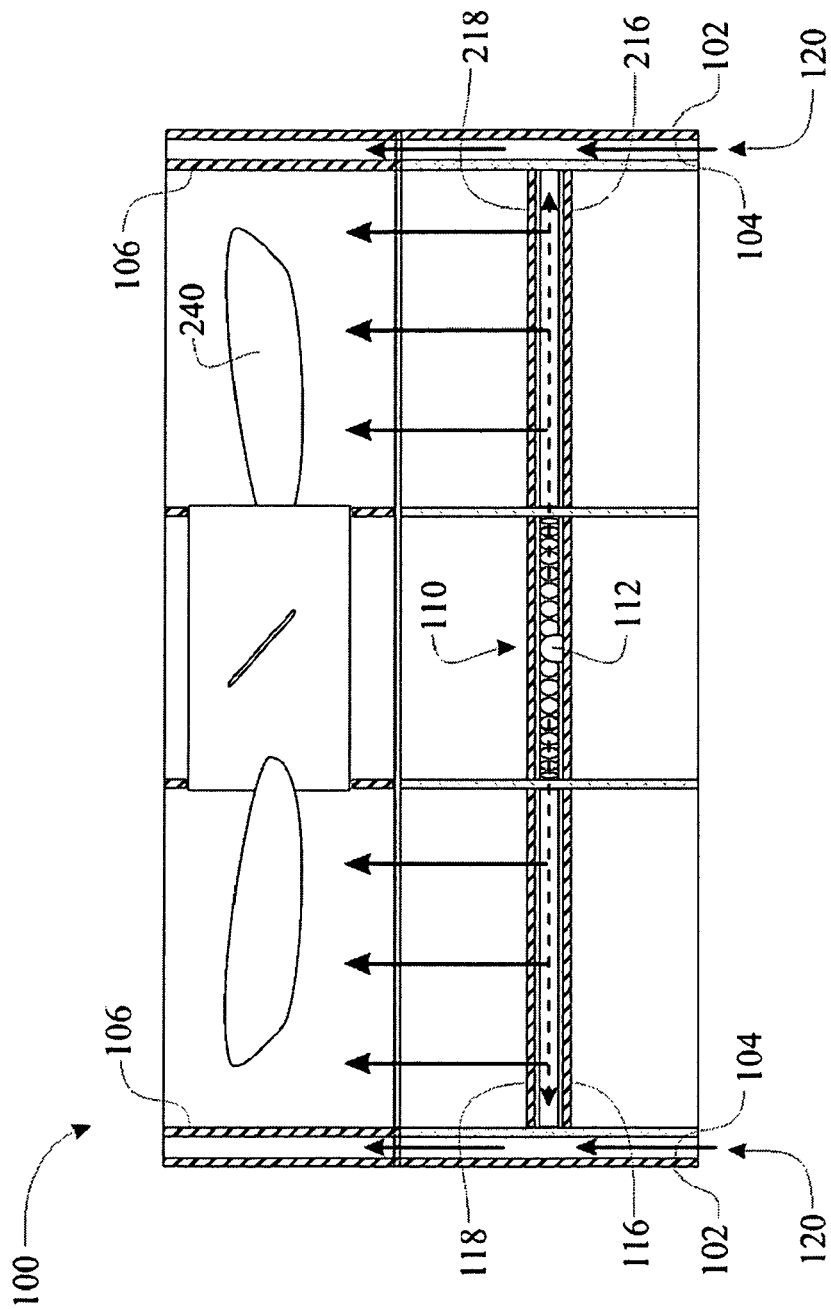
FIG. 16 presents a sectional side view of a fluid quality monitoring apparatus similar to the monitor of FIG. 1, illustrating a second exemplary embodiment of the flow driven power generator configuration.
Figure 17:
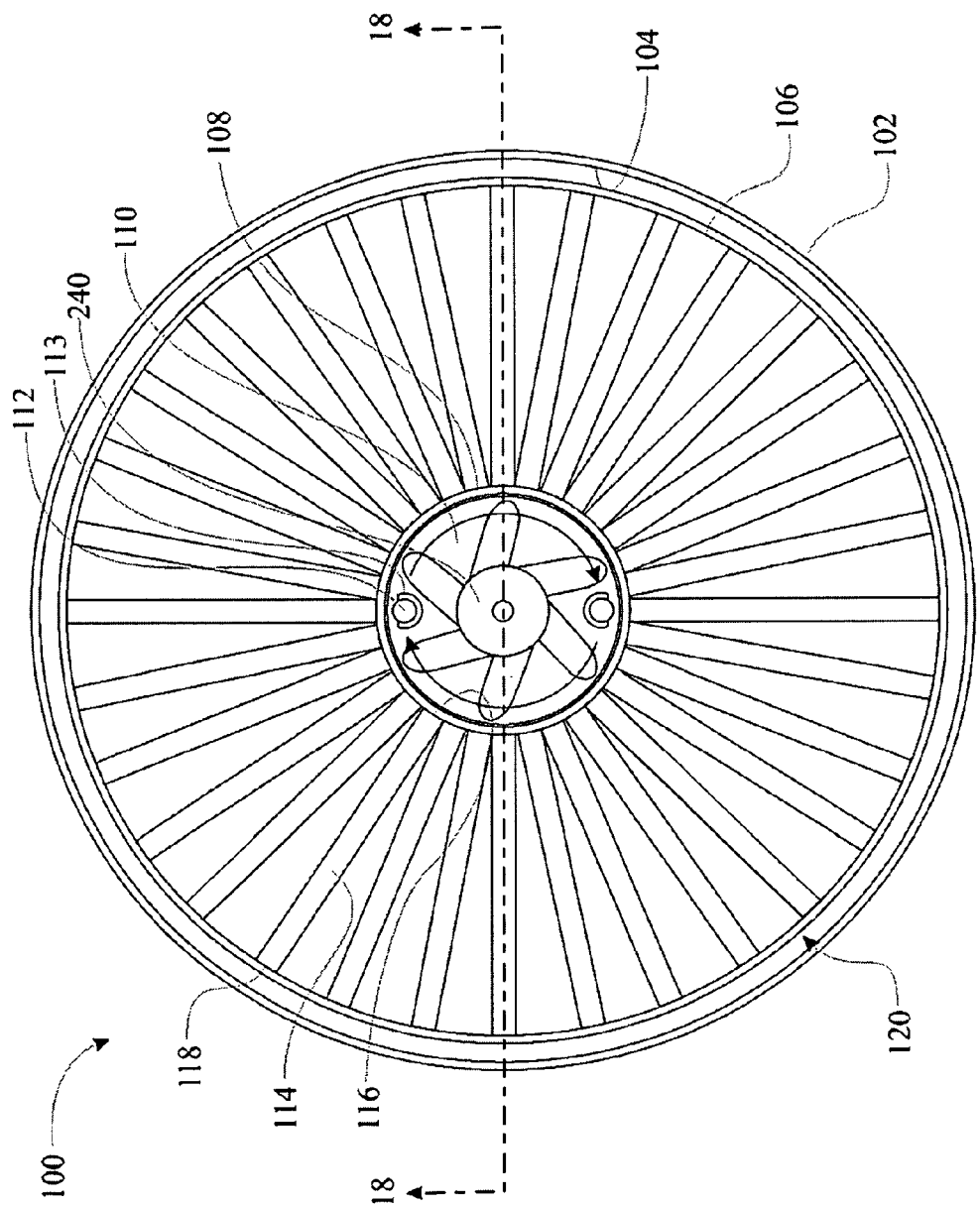
FIG. 17 presents a top planar view of the fluid quality monitoring apparatus introducing a wobble feature.

Power is required to generate the illumination source 112, 212 and operate the photo receptive surface 104. An illumination source collimator 113 can be assembled about any illumination source 112 to direct the emitted light in a desired direction as shown in FIG. 17. The illumination source 112, 212 can be encapsulated between an illumination management lower substrate 216 and an illumination management upper substrate 218. Fluid flow ports can be formed between the illumination management lower substrate 216 and the illumination management upper substrate 218. One such means to providing power is via an external power source and conveying the power to the illumination source. Another option is the incorporation of a battery or stored power cell. Yet, another option is the incorporation of a flow driven generator 240 (FIG. 13). The fluid flows through the interior flow ports 214 (or similar) causing the flow driven generator 240 to rotate. The resulting rotation of the flow driven generator 240 generates power to the fluid condition photovoltaic monitoring apparatus 100/200. The flow driven generator 240 can be placed parallel to the illumination assembly (FIG. 14), upstream (not shown, but understood) of the fluid flow, centered (FIG. 15), or downstream (FIG. 16) of the fluid flow. Additionally, the flow driven generator 240 can be used to monitor, limit, or control the fluid flow. Electrical energy generated by the flow driven generator 240 can be used to monitor the fluid flow, as the faster the flow driven generator 240 rotates, the greater the current or voltage output. The output can be used to determine the flow rate, in which a speed control (such as an electrically operated braking system) can be implemented, limiting the rotational speed of the flow driven generator 240. The reduced speed blocks the fluid flow thus reducing it. A magnet 250 or an electro magnet 252 can be incorporated, preferably assembled within the is fluid flow path, as a means for gathering any magnetic particles that may contaminate the fluid. By pulsing the electro magnet 252, the electro magnet 252 can orient any magnetic particles, and then release them into the fluid in a desired orientation.

Figure 18:
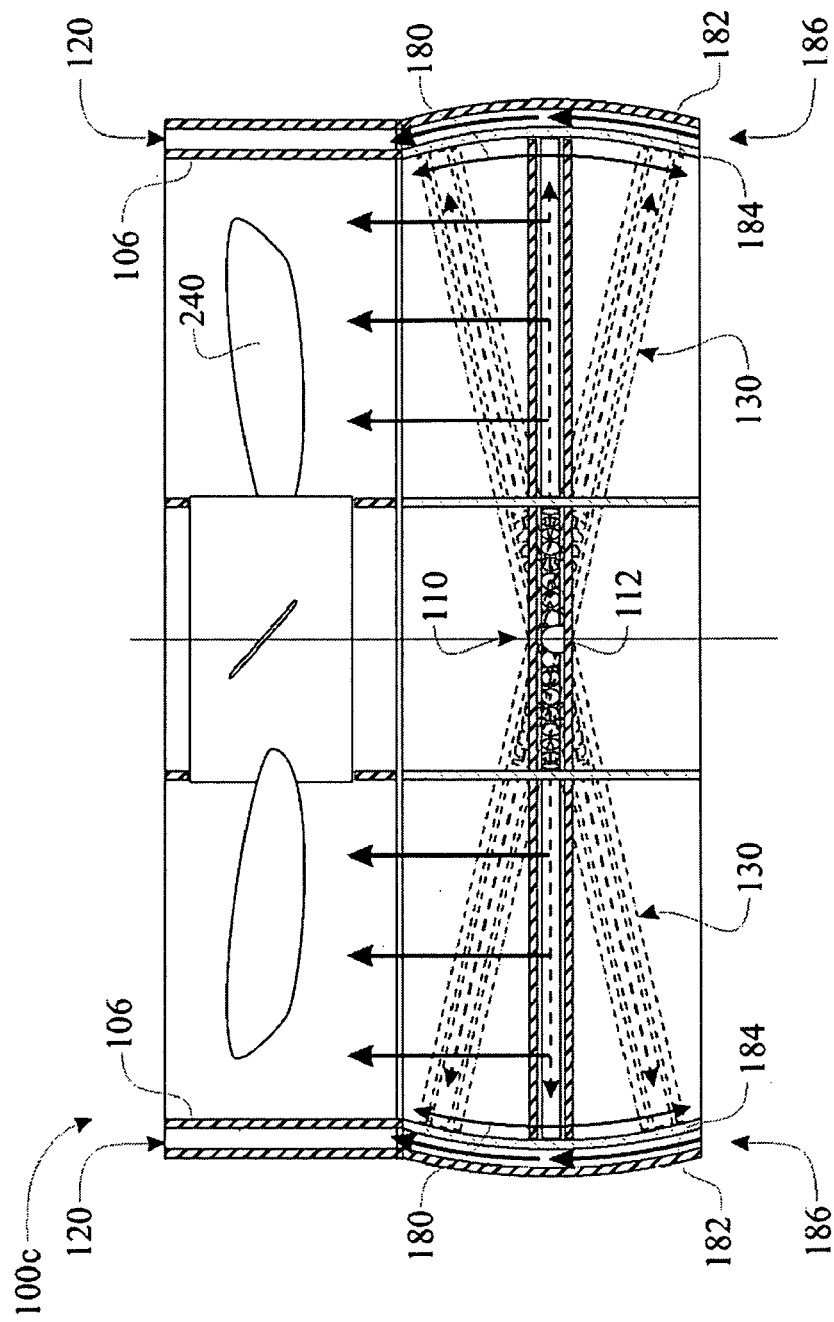
FIG. 18 presents a sectional view of the fluid quality monitoring apparatus taken along sectioning line 18-18 of FIG. 17.
Figure 19:
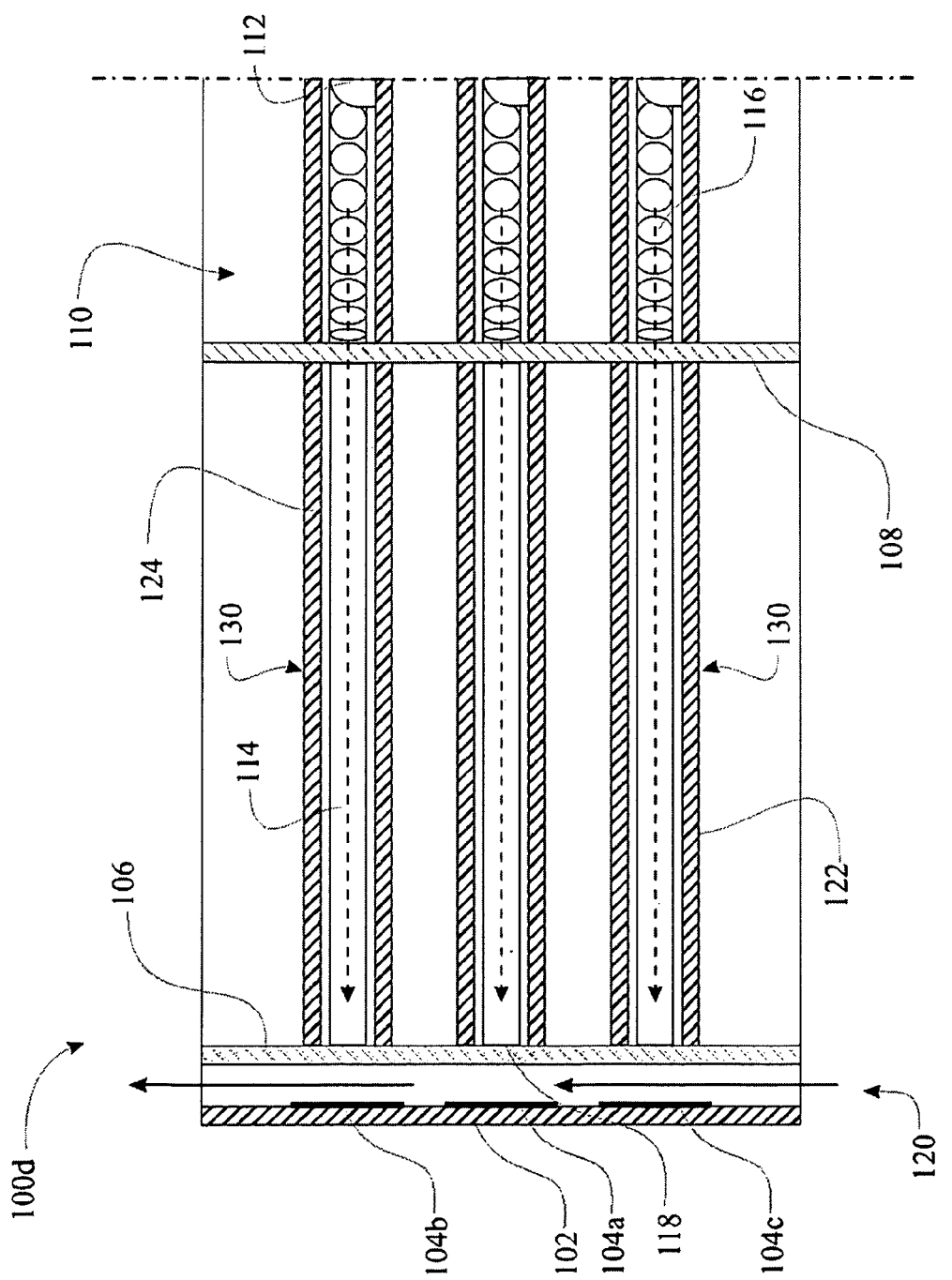
FIG. 19 presents a stacked series of illumination distribution assemblies targeting independent photosensitive receiving sections.
Figure 20:
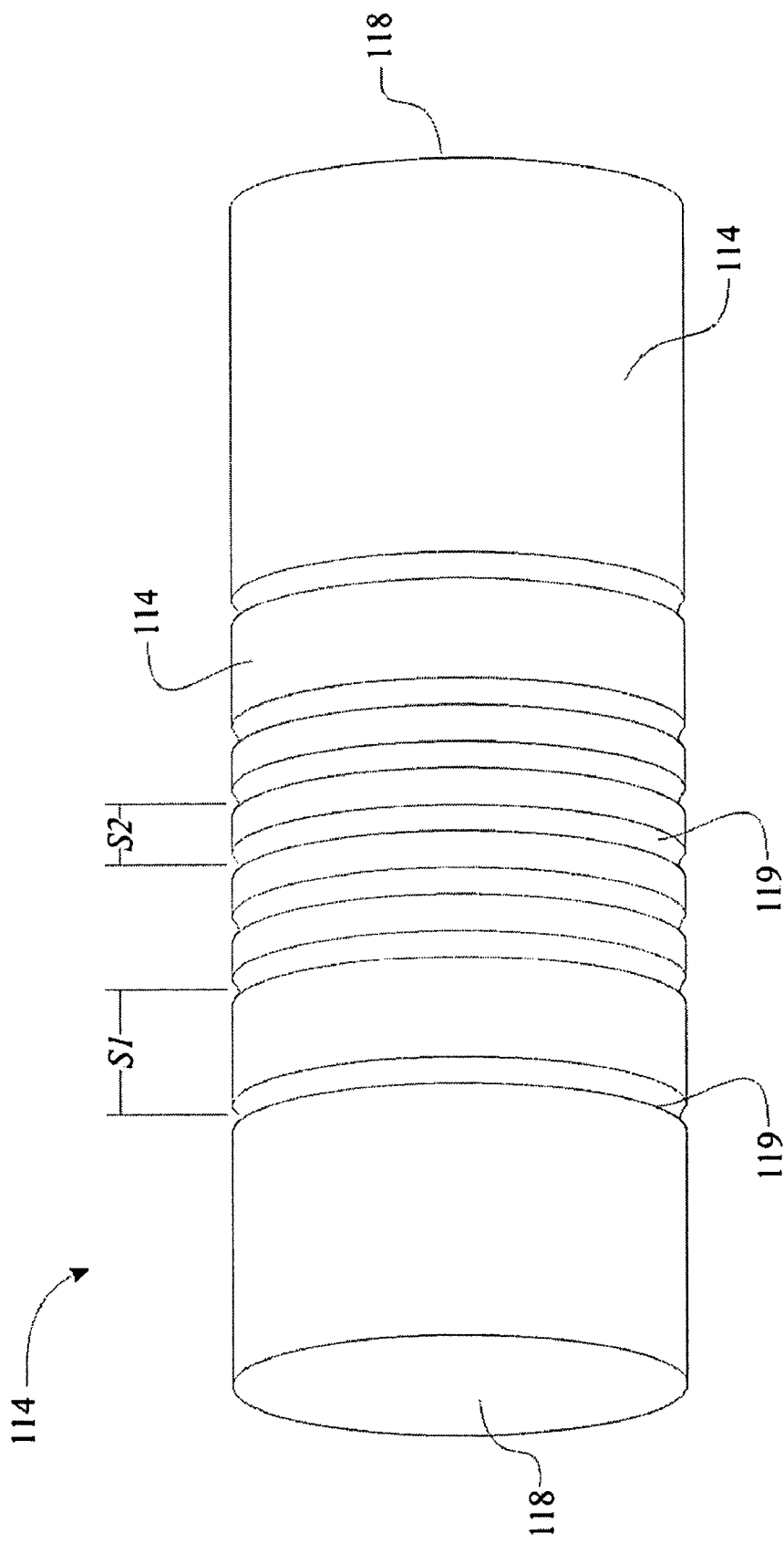
FIG. 20 presents a fiber optic material having a plurality of grooves forming a wavelength filter.

Several exemplary embodiments are presented illustrating optional features for the light sensing process. A first optional feature incorporates a pivoting motion 180 into the assembly of the illumination distribution assembly 130 to the pivoting light photovoltaic monitoring apparatus 100c as illustrated in FIG. 18. The pivoting motion 180 can be driven by the fluid flow interaction with the flow driven generator 240. The outer edge of the illumination distribution assembly 130 rides along an inner wall of an arched fluid monitoring flow channel 186, wherein the arched fluid monitoring flow channel 186 is formed having a radius substantially the same as a radius of the illumination distribution assembly 130. An arched photo receptive surface 184 is disposed upon an inner surface of an arched fluid testing exterior casing 182. The arched fluid monitoring flow channel 186 would be in fluid communication with the fluid monitoring flow channel 120. The pivoting motion 180 can be provided via any known mechanical or fluid interface. Examples include a radial floating layer and a gimbaled axle. A second optional feature provides a plurality of photo receptive surface 104 having different textures or other properties, each being positioned proximate a respective light emitting assembly illumination distribution assembly 130 as illustrated in FIG. 19. An exemplary distribution of the photo receptive surface 104 utilizes the photo receptive surface 104a, photo receptive surface 104b, and photo receptive surface 104c previously presented herein. Another exemplary distribution could utilize a series of photo receptive surface 104 having different photosensitive properties. A third exemplary embodiment provides a frequency filter within the fiber optic strand 114 as illustrated in FIG. 20. The frequency filter is designed extracting certain undesirable frequencies such to monitor certain properties of the fluid. An exemplary filter incorporates a series of filtering grooves 119 formed at predetermined spacings S1, S2. The spacings S1, S2 are set at a ratio of the wavelength of the frequency, thus providing a filter or plurality of is filters.

Figure 21:
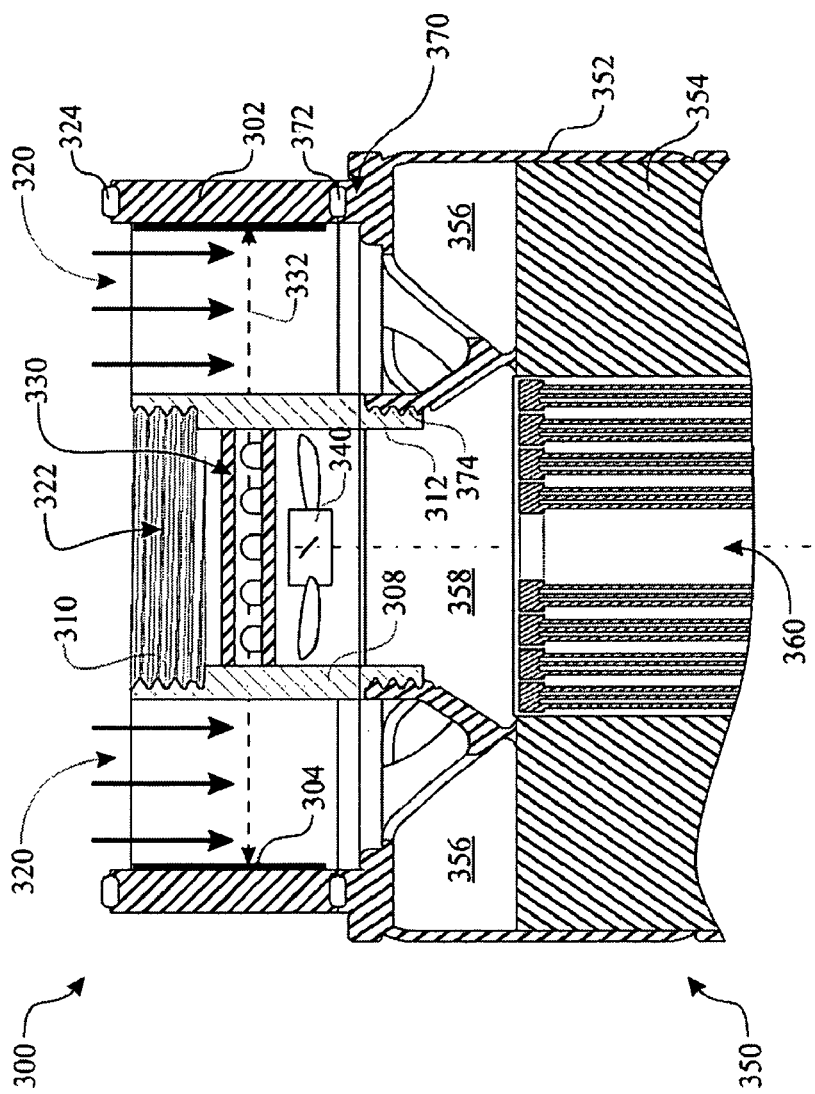
FIG. 21 presents a quality monitoring apparatus integrated between a filter and a filter mounting bracket.

A fluid condition photovoltaic monitoring apparatus 300 can be secured within a fluid filtration assembly between a filter assembly 350 and a bracket (not shown but well understood), such as the exemplary embodiment presented in FIG. 21. The fluid condition photovoltaic monitoring apparatus 300 includes the features previously presented, while further incorporating a bracket mounting interface 310 and a filter mounting interface 312. The bracket mounting interface 310 and filter mounting interface 312 can optionally be incorporated into an inner tubular structure 308 as shown. An illumination distribution assembly 330 provides a light transmission 332 that is directed through the translucent material of the inner tubular structure 308 and towards a photo receptive surface 304 applied to an inner wall of the outer tubular structure 302. The photo receptive surface 304 provides an output indicative of the level of light received after being transmitted through a fluid, as the fluid passes through a fluid monitoring flow channel 320. The fluid monitoring flow channel 320 being formed between the inner wall of the outer tubular structure 302 and an outer wall of the inner tubular structure 308. A flow driven generator 340 can be placed within an interior flow channel 322, wherein the flow driven generator 340 provides electric power from the fluid flow. It is understood that the light source can be assembled in any configuration capable of providing light to the photo receptive surface 304. Further, the photo receptive surface 304 can be assembled to any reasonable location within any fluid flow path, such to provide a monitoring process of the fluid.

The filter assembly 350 is an exemplary filter, including the general components of a fluid filter, such as a filter casing 352 encasing a filter material 354. The filter assembly 350 is secured to a fluid interface such as a bracket or the filter assembly 350 via a filler mounting interface 374. The filter mounting interface 374 forms a fluid flow channel within the internal portion of the filter assembly 350 and a filter seal 327 (being assembled to a filter outer seal ring 370) forms an outer barrier of an outer fluid flow channel. Fluid entering the outer fluid flow channel is distributed within the filter via a filter entrance manifold 356. Fluid flows via a filter return flow 360 and is collected within a filter exit orifice 358, then returns the fluid to the lubrication system.

The fluid condition photovoltaic monitoring apparatus 300 would be assembled between the filter assembly 350 and a filter mounting bracket (not shown). The fluid condition photovoltaic monitoring apparatus 300 assembles to the filter assembly 350 via an engagement between the filter mounting interface 374 and the filter mounting interface 312. A filter seal 327 provides an outer seal between the two outer members. The fluid condition photovoltaic monitoring apparatus 300 assembles to the filter mounting bracket via an engagement between the bracket mounting interface 310 and the mating member of the filter bracket. A bracket seal 324 provides an outer seal between the two outer members.

The fluid condition photovoltaic monitoring apparatus 300 shown is only representative, wherein the present invention can be integrated into any fluid monitoring system, such as a lubrication filtration system (as shown), a blood (or other bio-fluid) monitoring system, a water filtration or monitoring system, a fuel filtration or monitoring system, a gas monitoring system, and the like.

The fluid monitoring flow channel 120 can include features to direct the fluid flow in a linear flow motion, a spiraling flow motion, varying in flow rates, flow pressures, general direction, and the like. This can be used for any integrated detection sensing devices.

The apparatus 100 can include an inlet and outlet configuration being removably attachable to a fluid reclamation system. One such design would include the commonly known components of a filter interface on a first side and a filter bracket on the opposing side.

The teachings present a configuration locating the illumination source on an interior side of the tubular structures. It is recognized by the inventor that the illumination source can be positioned on an exterior of the outer tubular structure and the sensing material can be placed on the outside of the inner tubular structure to achieve the same function, maintaining the spirit and intent of the present invention.

The above description is considered that of the preferred embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

We claim:

1. A fluid quality monitoring apparatus, the apparatus comprising:

an outer tubular structure having an exterior wall surface and an interior wall surface;

an inner tubular structure disposed within a hollow region formed within the outer tubular structure, the inner tubular structure having an exterior wall surface, wherein the inner tubular structure is light permissive;

a fluid passageway formed between the interior wall surface of the outer tubular structure and the exterior wall surface of the inner tubular structure for free flowing conveyance of a subject fluid for testing;

a photovoltaic material applied to a majority of a circumferential section of either surface of the outer tubular structure;

an illumination source assembly comprising an illumination source and a plurality of fiber optic strands, wherein emitting ends of the fiber optic strands are located proximate the inner tubular structure interior wall surface, wherein the fiber optic strands transfer emitted light from the illumination source to the emitting ends and projects the light from the emitting ends, through the subject fluid, and towards the photovoltaic material; and an output conduit providing electrical communication for an electrical output signal from the photovoltaic material to a quality monitoring apparatus.

2. A fluid quality monitoring apparatus as recited in claim 1, the apparatus further comprising a diffraction grating provided upon the photovoltaic material.

3. A fluid quality monitoring apparatus as recited in claim 1, wherein the illumination source assembly is positioned within an interior of the inner tubular structure;

wherein the plurality of fiber optic strands is arranged in a radial pattern each strand extending from a centrally located light source having the emitting ends positioned about a portion of a perimeter of the surface of the inner tubular structure providing a light conduit between the illumination source and a location proximate the inner tubular structure; and wherein the photovoltaic material is applied to a surface of the outer tubular structure about a portion of a perimeter of the surface of the outer tubular structure being relational to the positioned emitting ends.

4. A fluid quality monitoring apparatus as recited in claim 1, the monitoring apparatus further comprising a substance control sample of the subject fluid enclosure positioned within a portion of the flow passageway, wherein said substance control sample is a sample of said subject fluid having a known quality level.

5. A fluid quality monitoring apparatus, the apparatus comprising:

an outer tubular structure having an exterior wall surface and an interior wall surface;

an inner tubular structure disposed within a hollow region formed within the outer tubular structure, the inner tubular structure having an exterior wall surface and an interior surface, wherein the inner tubular structure is light permissive;

a free flowing fluid passageway formed between the interior wall surface of the outer tubular structure and the exterior wall surface of the inner tubular structure for conveyance of a subject fluid for testing;

a fluid inlet port located at an entrance end of the fluid passageway and a fluid exit port located at an exit end;

a photovoltaic material applied to either outer tubular structure wall surface;

an illumination source assembly comprising an illumination source and a plurality of fiber optic strands, wherein the illumination source assembly is located within a hollow region formed by the inner tubular structure and the emitting ends of the fiber optic strands are located proximate the inner tubular structure interior surface, wherein the fiber optic strands transfer emitted light from the illumination source to the emitting ends and projects the light from the emitting ends, through the subject fluid, and towards the photovoltaic material; and an output conduit providing electrical communication for an electrical output signal from the photovoltaic material to a quality monitoring apparatus.

6. A fluid quality monitoring apparatus as recited in claim 5, the apparatus further comprising a diffraction grating provided upon the photovoltaic material.

7. A fluid quality monitoring apparatus as recited in claim 5, the apparatus further comprising a generator having a fluid lubrication system, wherein the fluid lubrication system is in fluid communication with the fluid flow passageway.

8. A fluid quality monitoring apparatus as recited in claim 5, the apparatus further comprising at least one interior flow port passing through the illumination source assembly.

9. A fluid quality monitoring apparatus as recited in claim 8, the apparatus further comprising a generator having a fluid lubrication system, wherein the fluid lubrication system is in fluid communication with the fluid flow passageway and the at least one interior flow port.

10. A fluid quality monitoring apparatus as recited in claim 5, wherein the plurality of fiber optic strands is arranged in a radial pattern, each strand extending from a centrally located light source having the emitting ends positioned about a portion of a perimeter of the surface of the inner tubular structure providing a light conduit between the illumination source and a location proximate the inner tubular structure; and wherein the photovoltaic material is applied to a surface of the outer tubular structure about a portion of a perimeter of the surface of the outer tubular structure being relational to the positioned emitting ends.

11. A fluid quality monitoring apparatus as recited in claim 5, wherein the illumination source assembly is assembled to the monitoring apparatus in a manner allowing the illumination source assembly to wobble.

12. A fluid quality monitoring apparatus as recited in claim 5, the photovoltaic material is segregated into a plurality of sections, wherein at least two sections sense different properties.

13. A fluid quality monitoring apparatus, the apparatus comprising:

an outer tubular structure having an exterior wall surface and an interior wall surface;

an inner tubular structure disposed within a hollow region formed within the outer tubular structure, the inner tubular structure having an exterior wall surface and an interior wall surface wherein the inner tubular structure is light permissive;

a free flowing fluid passageway formed between the interior wall surface of the outer tubular structure and the exterior wall surface of the inner tubular structure for conveyance of a subject fluid for testing;

a fluid inlet port located at an entrance end of the fluid passageway and a fluid exit port located at an exit end;

a photovoltaic material applied to either outer tubular structure wall surface;

an illumination source assembly comprising an illumination source and a plurality of fiber optic strands, wherein emitting ends of the fiber optic strands are located proximate the inner tubular structure interior surface, wherein the fiber optic strands transfer emitted light from the illumination source to the emitting ends and projects the light from the emitting ends, through the subject fluid, and towards the photovoltaic material;

wherein the illumination source assembly is located within an interior region of the inner tubular structure;

an output conduit providing electrical communication for an electrical output signal from the photovoltaic material to a quality monitoring apparatus; and a coupling interface for integrating the fluid quality monitoring apparatus into fluid communication with an engine lubrication filtration system.

14. A fluid quality monitoring apparatus as recited in claim 13, the apparatus further comprising a diffraction grating provided upon the photovoltaic material.

15. A fluid quality monitoring apparatus as recited in claim 13, wherein the plurality of fiber optic strands is arranged in a radial pattern, each strand extending from a centrally located light source having the emitting ends positioned about a portion of a perimeter of the surface of the inner tubular structure providing a light conduit between the illumination source and a location proximate the inner tubular structure; and wherein the photovoltaic material is applied to a surface of the outer tubular structure about a portion of a perimeter of the surface of the outer tubular structure being relational to the positioned emitting ends.

16. A fluid quality monitoring apparatus as recited in claim 13, the apparatus further comprising at least one flow port passing through the illumination source assembly.

17. A fluid quality monitoring apparatus as recited in claim 16, the apparatus further comprising a generator having a fluid lubrication system, wherein the fluid lubrication system is in fluid communication with the fluid flow path.

18. A fluid quality monitoring apparatus as recited in claim 13, wherein the outer tubular structure is not parallel with the inner tubular structure, providing a change in flow rates.

19. A fluid quality monitoring apparatus as recited in claim 13, the apparatus further comprising:

an illumination management lower substrate located within an interior portion of the inner tubular structure on a first side of the illumination source assembly;

an illumination management upper substrate within an interior portion of the inner tubular structure on a side opposing the first side of the illumination source assembly;

at least one interface located between the illumination management upper substrate and the illumination management lower substrate;

wherein the illumination management upper substrate, the illumination management lower substrate, and the at least one interface disposed there between provides an encapsulation isolating the illumination source assembly from any fluid.

* * * * *